US012788627B2

(12) United States Patent
Hiebert

(10) Patent No.: US 12,788,627 B2
(45) Date of Patent: *Nov. 10, 2026

(54) PATIENT THERMAL REGULATION SYSTEMS

(71) Applicant: Eugene Lloyd Hiebert, Salem, OR (US)

(72) Inventor: Eugene Lloyd Hiebert, Salem, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/380,669

(22) Filed: Nov. 5, 2025

(65) Prior Publication Data

US 2026/0060838 A1 Mar. 5, 2026

Related U.S. Application Data

(63) Continuation of application No. 19/071,249, filed on Mar. 5, 2025, now Pat. No. 12,485,039, which is a continuation of application No. 18/916,470, filed on Oct. 15, 2024, now Pat. No. 12,268,629, which is a continuation of application No. 18/368,131, filed on Sep. 14, 2023, now Pat. No. 12,150,889, which is a continuation of application No. 17/095,116, filed on Nov. 11, 2020, now Pat. No. 11,786,395.

(60) Provisional application No. 62/977,620, filed on Feb. 17, 2020, provisional application No. 62/935,784, filed on Nov. 15, 2019.

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/006* (2013.01); *A61F 2007/0258* (2013.01)

(58) Field of Classification Search
CPC ........ A61F 2007/006; A61F 2007/0228; A61F 2007/0258; A61F 7/0085; A61F 7/0097; A61F 7/02
See application file for complete search history.

(56) References Cited

U.S. PATENT DOCUMENTS

| | | | | |
|---|---|---|---|---|
| 8,151,391 | B2 | 4/2012 | Frias | |
| 2002/0166168 | A1 | 11/2002 | Weedling et al. | |
| 2017/0027743 | A1* | 2/2017 | McGregor | A61F 7/02 |
| 2018/0028702 | A1* | 2/2018 | Lewis | A61L 2/22 |
| 2018/0242753 | A1 | 8/2018 | Ghanei et al. | |

* cited by examiner

*Primary Examiner* — Tigist S Demie
(74) *Attorney, Agent, or Firm* — Klarquist Sparkman, LLP

(57) ABSTRACT

Disclosed herein are devices and systems that conduct temperature-controlled air through one or more enclosed chambers that are placed adjacent to a patient to help control the patient's temperature without blowing air directly on the patient. In some embodiments, the enclosed chamber has an air inlet and an air outlet and a defined air flow pathway therebetween. Air exiting the device can be directed away from the patient. The flowing air can be any desired temperature to help warm or cool a patient. The patient can be a human or animal, for example.

15 Claims, 14 Drawing Sheets

PATIENT THERMAL REGULATION SYSTEMS

CROSS-REFERENCE TO RELATED APPLICATIONS

This application is a continuation of U.S. patent application Ser. No. 19/071,249, filed Mar. 5, 2025, which is a continuation of U.S. patent application Ser. No. 18/916,470, filed Oct. 15, 2024, now U.S. Pat. No. 12,268,629, which is a continuation of U.S. patent application Ser. No. 18/368,131, filed Sep. 14, 2023, now U.S. Pat. No. 12,150,889, which is a continuation of U.S. patent application Ser. No. 17/095,116, filed Nov. 11, 2020, now U.S. Pat. No. 11,786,395, which claims the benefit of U.S. Provisional Patent Application No. 62/977,620, filed Feb. 17, 2020, and U.S. Provisional Patent Application No. 62/935,784, filed Nov. 15, 2019, each of which is incorporated by reference herein.

FIELD

This application concerns devices and systems for thermally regulating patients in a medical setting using flowing air.

SUMMARY

Disclosed herein are devices and systems that conduct temperature-controlled air through one or more enclosed chambers that are placed adjacent to a patient to help control the patient's temperature without blowing air directly on the patient. In some embodiments, the enclosed chamber has an air inlet and an air outlet and a defined air flow pathway therebetween. Air exiting the device can be directed away from the patient. The devices can include a crush-resistant but flexible air-flow layer of material inside the enclosure that allows airflow even when a patient is laying on the device. A cushioning layer can also be included overlaying the air-flow layer. The flowing air can be any desired temperature to help warm or cool a patient. The patient can be a human or animal, for example.

DETAILED DESCRIPTION

Figure 1:
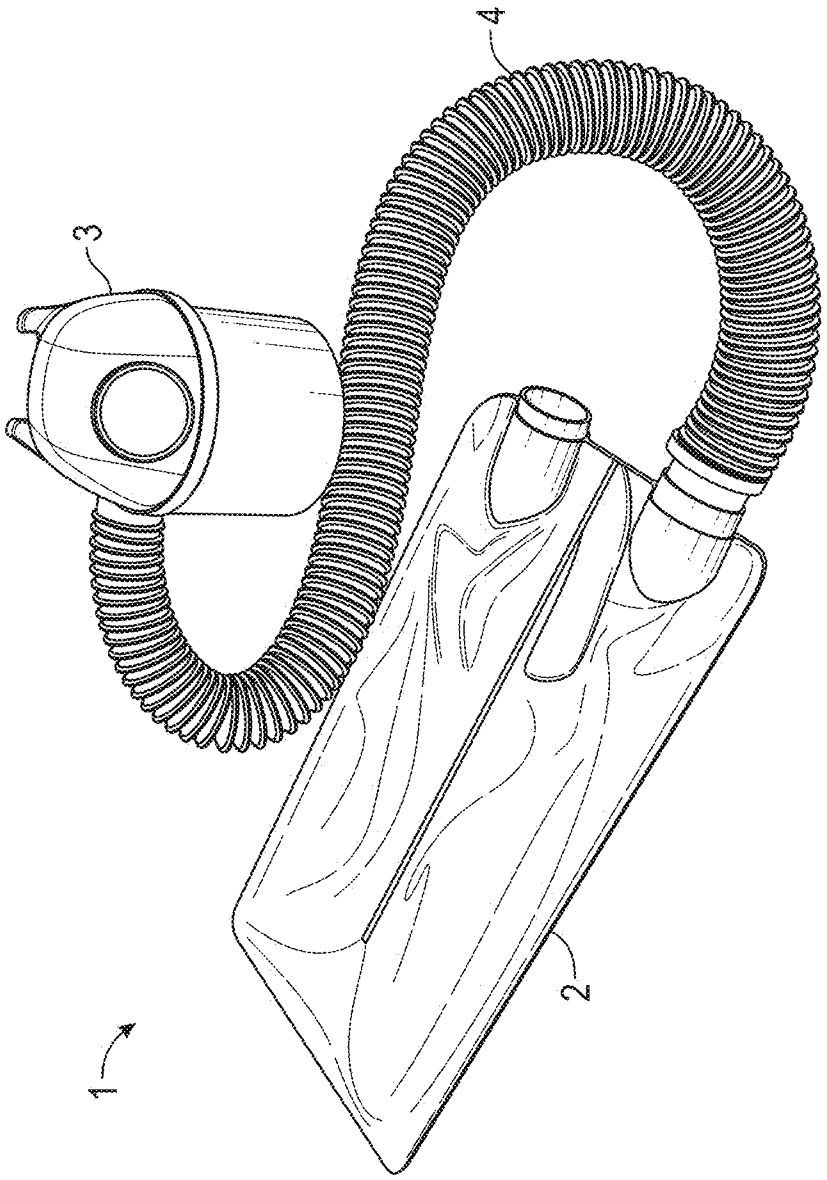
FIG. 1 shows an exemplary system that includes a thermal regulation enclosure, or pad, with an inlet and an outlet and an airflow pathway therebetween, and a conduit coupling the inlet to an air blower.

Hypothermia is the most common thermal consequence of general anesthesia. Millions of humans and animals are anesthetized every year with anesthesia and surgical professionals struggling to maintain normothermia and the consequent deleterious physiological effects of hypothermia. Hypothermia is defined as the body temperatures below 35 degrees Centigrade for human adults, below 36 degrees Centigrade for human infants, and between 35.8 degrees Centigrade and 37 degrees Centigrade for dogs and cats.

The majority of patient heat loss during anesthesia and surgery is through the skin by the processes of radiation, conduction and convection. Radiation is the major source of heat loss in surgical patients in which infrared radiant energy is transferred from the relatively warm patient to the environment. Conduction refers to the direct flow of heat from the body to the surrounding air, fluids or solid materials such as a metal surgical table. Convection involves the physical movement of ambient air or fluids by which body heat is removed from the patient. These three heat loss processes occur as core body heat redistributes to the periphery and the skin surface as a consequence of anesthetic induced peripheral vasodilation and depression of the hypothalamic thermoregulatory centers.

Hypothermia occurs in three phases following anesthetic induction.

Phase 1: In the first hour of anesthesia there is a rapid decline in body temperature as a consequence of anesthetic induced peripheral vasodilation and lowering of the temperature threshold in the hypothalamus preventing the institution of normal physiologic thermoregulatory mechanisms. These processes allow a redistribution of body heat from the body core to the periphery where heat is lost primarily through the skin by radiation and convection.

Phase 2: Over the next two hours of anesthesia, body temperature declines in a slower linear fashion as heat loss exceeds heat production. This occurs as a consequence of a decrease in metabolism and inhibition of heat production by thermoregulatory mechanisms in the hypothalamus by anesthetic drugs.

Phase 3: Over the next three to four hours of anesthesia a core body temperature plateau is reached after which temperature stabilizes and remains relatively unchanged as a thermal steady state is achieved.

Prolonged hypothermia can lead to significant morbidity and mortality causing health care professionals to maintain body temperature during anesthesia as normothermic as possible. Deleterious consequences of hypothermia can include cardiac arrhythmias, increased peripheral vascular resistance (vasoconstriction), decreased oxygen uptake by red blood cells, coagulopathy and platelet dysfunction, postoperative protein catabolism and stress response, altered mental status, impaired renal function, decreased drug metabolism, poor wound healing, increased surgical site infections, and death.

Exemplary Patient Thermal Regulation Systems

One exemplary method of patient warming/cooling is by forced warm/cool air. In the case of warming, an electrical warm air blower is connected to a disposable blanket by a flexible hose or conduit. The disposable blanket has multiple channels so that air is directed throughout the blanket. The blanket has multiple pin sized holes on one surface of the blanket that is adjacent to the patient so that the warmed air can escape from the blanket through the pin sized holes to thereby blow the warmed air onto the patient. The disposable blanket can be placed over the superior aspect of the patient to attempt to warm the patient. The blanket can also be placed underneath the patient in an attempt to warm the patient's posterior aspect. With the blanket being on the superior aspect of the patient there is minimal obstruction to air flow through the pin sized holes.

However, when the patient is laying on the blanket or the blanket is underneath the patient, all the pin sized holes upon which the patient is laying are blocked so that warm air cannot flow through these obstructed holes to warm the patient. In addition, air channels within the blanket can be crushed and blocked such that air flow through the blanket is restricted. The posterior or dependent aspect of the patient, therefore, cannot be warmed with forced air warming. Only pin sized holes which are not blocked by the patient's anatomy, such as along the sides or lateral aspects of the patient, will allow egress of warmed air. There is, therefore, little true underbody forced air warming. The term underbody can also be stated as the dependent portion of the body. This is defined as the area of the body which is in contact with the underlying supporting surface.

Since the warm air which is being blown through the blanket and ultimately through the pin sized holes is not sterile the opportunity for a surgical wound infection is very real and has been litigated. The source of the air which is blown through the warm air blower is usually the air from the floor of the operating room where the warm air blower is situated. Sometimes the blower is mounted on a pole for hanging intravenous fluids. None of these sources of air are sterile. A surgical site infection can occur when a surgical patient with an open surgical wound is laying on a disposable warming blanket with non-sterile air blowing around the patient's body and up toward the open surgical site. Similarly, when non-sterile warm air from a warming blanket is blowing on the superior aspect of the patient as for example on the chest and arms when the abdomen is the surgical site.

The egress of warm air from the pin sized holes of the disposable warming blanket coming up and around a patient from an underbody warming blanket and the warm air egressing from the pin sized holes in a warming blanket overlying the patient has been shown to disturb the laminar flow of sterile air in the operating room. During the performance of total joint procedures such as a hip joint replacement with a prosthesis, sterile air is forced over the surgical field either from above or from one side of the operating room in a laminar flow pattern to decrease the incidence of infection of the newly placed joint prosthesis. This laminar flow of air has been shown to be disturbed by the flow of air from the forced air warming blankets thereby disturbing the sterile field.

The ambient temperature in an operating room is always below body temperature. Consequently, when a patient, scantily clad or even nude, is laying on an operating table in a cold operating room, the patient is exposed to this colder ambient temperature. It is, therefore, virtually impossible for the patient not to have air around its body that is at ambient room temperature. The warming blanket does not insulate the patient from the temperature of the ambient air and does not eliminate this ambient air between the body and the warming blanket. The warm air egressing from the pin sized holes of the warming blanket, therefore, mixes with the cooler ambient room air around the body. The warmer air egressing from the warming blanket is, therefore, diluted or cooled by the cooler air surrounding the patient and consequently not delivering the warming temperature that was intended.

Simple forced air warming systems cannot warm the dependent aspects of a patient's body. They can only warm non-dependent aspects of a patient's body. For example, when the patient is laying in the supine position and the patient is undergoing an abdominal surgical procedure, the only portion of the body which can be warmed are the superior aspects of the chest, arms and legs. This is a significant flaw in patient warming since the majority of patient blood flow is in the dependent portion of the patient's body and internal organs due to the effect of gravity. In the case of the patient in the supine position the majority of the patient's blood flow will be in the retroperitoneal or posterior aspect of the patient's body. The current forced air warming systems are, therefore, warming only the non-dependent aspects of the body with less blood flow than the dependent aspects of the body. The transfer of heat from an overlying warming blanket is, therefore, significantly inefficient because there is less blood flow close to the surface of the body to carry this transferred heat to the rest of the body.

Improved Patient Thermal Regulation Systems

Figure 2:
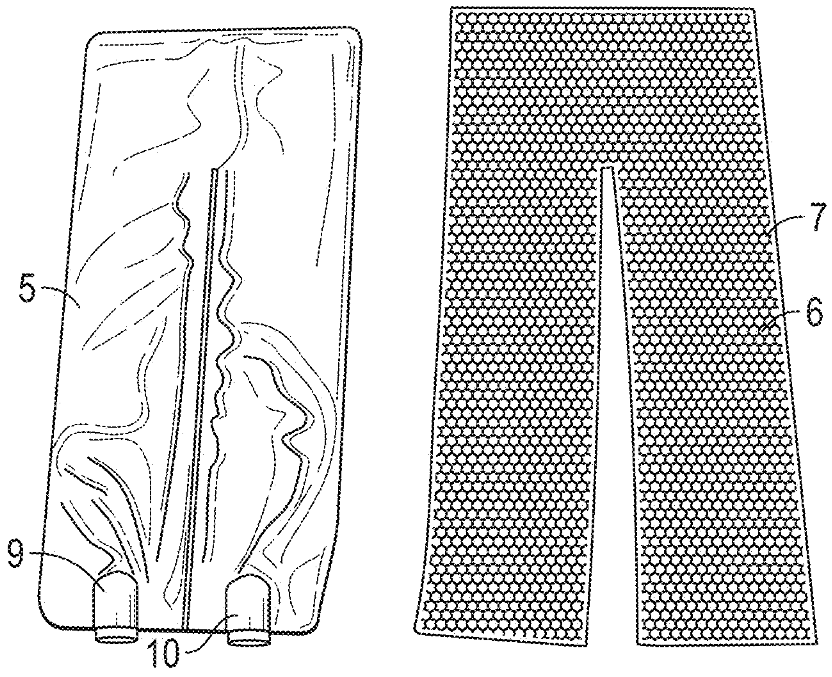
FIG. 2 shows the enclosure of FIG. 1 side-by-side with exemplary internal components that go inside the enclosure.
Figure 3:
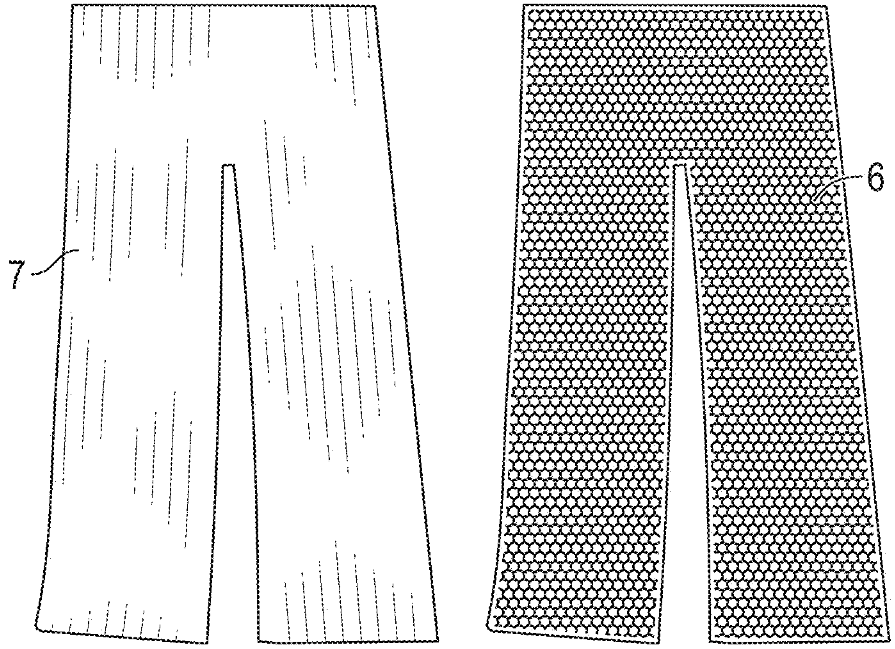
FIG. 3 shows the internal components of FIG. 2, which include an airflow layer and a resiliently compressible support layer.
Figure 4:
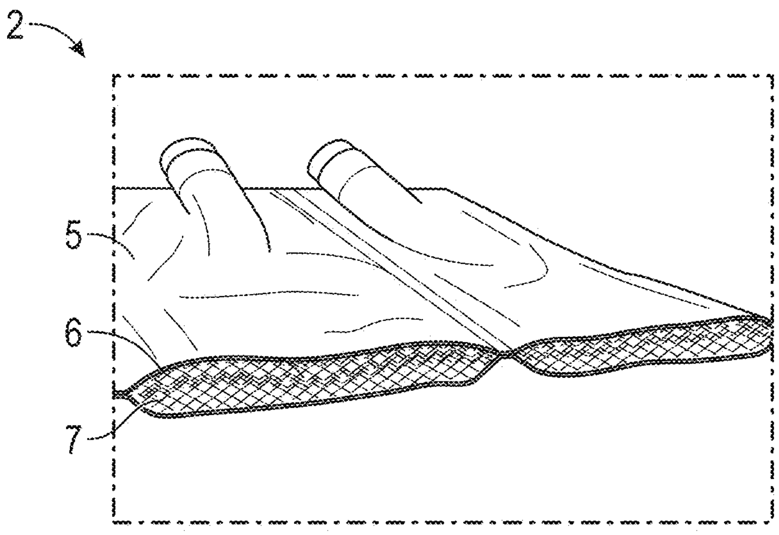
FIG. 4 shows a cross-section of the enclosure with the airflow layer and the support layers within.
Figure 5:
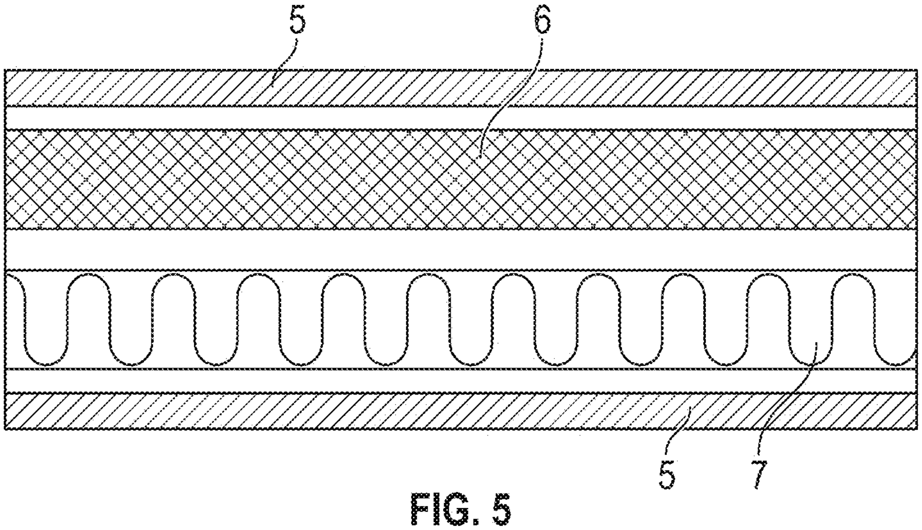
FIG. 5 is a schematic cross-sectional illustration showing the airflow layer and the support layer within the enclosure.

As illustrated in FIGS. 1-5, an improved patient thermal regulation system 1 can include a pad 2 comprising an enclosure having two flexible and supple surfaces of fluid and air impermeable material between which is other internal material or materials, at least one of which allows for air flow and is resistant to crushing when a patient lies on the pad. The pad 2 is coupled to an air blower, or pump, 3 via an air conduit 4. The internal material can be sufficiently firm to also allow for an unrestricted or less restricted flow path of air through the pad when a patient lays thereupon along with low resistance to air flow and minimal back pressure on the blower which blows warm air through the pad. As illustrated in FIGS. 2-4, the pad can include an impermeable outer enclosure 5, air inlet 9 and outlet 10, an internal air flow layer 7, and optionally a resiliently deformable cushion layer 6, and/or other components.

The air flow layer 7 besides being substantially resistant to crushing when a patient lies thereupon, can also be such that it is sufficiently flexible to prevent soft tissue injuries and pressure sores when a patient is laying on it for extended periods of time. Additionally, the internal material can also be such that it will flex with the surface whereupon it is laying or supported. To increase the property of being non-crushable and/or sufficiently flexible to prevent pressure sore or soft tissue injuries, in some embodiments several layers of materials may be included inside the enclosure where at least one (e.g., the air flow layer) is sufficiently non-crushable to allow for non-resistant air flow when the patient lies there upon, and at least one layer adjacent to the patient (e.g., the cushion layer) which is sufficiently flexible to prevent pressure sores or soft tissue injuries. The air-flow layer 7 can have a three-dimensional open-cell structure that allows air to flow through it in three dimensions, especially in both longitudinal and lateral directions of the enclosure, but also in a thickness direction. Materials that can be used for the internal materials are various and can include, but are not limited to, three dimensional fabrics, metal coiling, plastic coiling, plastic mesh, plastic tubing with concentric holes, reticulated foam, and combinations of these and other materials. Heat reflective materials such as aluminum foil or Mylar, for example, can be placed in the interior in such a manner that heat is reflected toward the patient and not allowed to be conducted to the underlying supporting surface.

To allow warmed air into the pad, an inlet port 9 can be provided to allow entry of air into the interior of the pad along with an outlet port 10 to allow for egress of the air from the pad. The inlet air can be directed in such a manner that the entire interior of the pad is filled with the warm/cool inlet air. To limit the inlet air from going directly to the outlet port, the device can include at least one circuitous air channel from the inlet port to the outlet port. This can be accomplished, for example, by creating a partial barrier to direct air flow between the inlet and outlet ports thereby forcing the inlet air to take a circuitous route from the inlet port to the outlet port. This can be done, for example, by sewing, gluing, heat sealing or radio-frequency welding the two external material surfaces together thereby creating a partial separative barrier or baffle between the inlet and outlet ports. For example, in an embodiment where the inlet and outlet ports are at the same end of a rectangular pad, the separative barrier can extend longitudinally from the inlet/outlet end toward the opposite end leaving a relatively shorter portion at the opposite end which is not sealed, thereby allowing inlet air to travel longitudinally toward the opposite end, around the end of the sealed separation and then longitudinally toward the outlet port. One or multiple barriers or baffles may be created to provide a circuitous air flow path from inlet to outlet. In such examples, a separation of the internal non-crushable material or other internal material can be made to accommodate the separative barrier or barriers. The inlet and outlet ports can be located on the under-side, top-side, lateral aspects, and/or end aspects of the pad and may be placed vertically, horizontally, and/or at an angle to allow for improved clinical application. The inlet and outlets may also be at opposite ends of the pad from each other or on the same end, as illustrated. The shape of the pad may be any shape that is clinically relevant or otherwise desirable. For example, the pad can be rectangular, square, circular or any other shape that may correspond to the underlying support surface, the shape of the patient, a particular surgical positioning, or any other shape that would make warming more clinically efficient.

Figure 6:
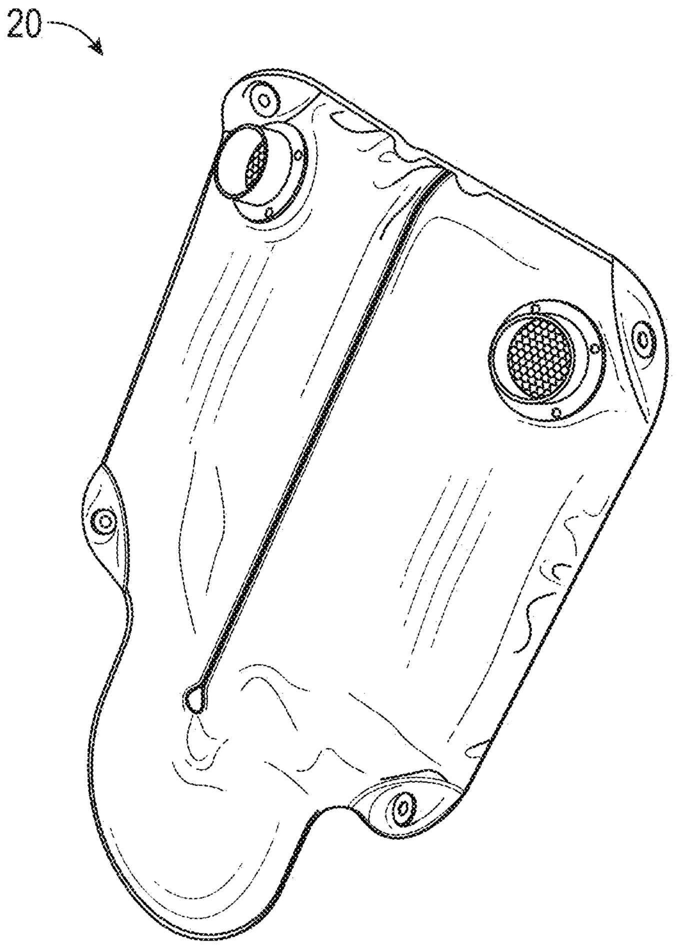
FIG. 6 shows another exemplary enclosure with an inlet and an outlet and an airflow pathway therebetween, and an airflow layer and a support layer within.

FIG. 6 shows another exemplary pad 20 that has a non-rectangular shape and includes grommets for attachment to other objects.

Warm air blowers often have a flexible conduit (see e.g., conduit 27 in FIG. 8) with a cuff/connector that allows for insertion into an orifice of some type. The inlet and/or outlet ports of the herein disclosed pads may, for example, comprise a flange collar, short pipe, a sleeve, elastic accommodation, and/or invagination of the external material into which the cuff of the blower conduit is inserted or any other method whereby the blower hose can be inserted into or connected to the pad and allow air flow into the pad. So that multiple different types of warm air blowers with different sized conduits and cuffs can be used with the disclosed pads, multiple sized adaptors may be provided to marry the blower conduit and the inlet port or a single cuff with an elastic sleeve to accommodate any sized hose. The external material itself can be configured so that it will accept any sized blower hose diameter. The adaptors may be secured together to prevent separation, for example, with elastic lanyards, a lanyard with cording that loops around each adaptor component, a snap lock that locks each adaptor component together, to name a few. The pad itself can have a sleeve incorporated into it at the time of manufacture, which may include elastics, ties, snaps, Velcro, or other attaching devices, which can be utilized to accommodate multiple sized warm air hoses. A cuff that fits into the inlet and outlet ports may have an adaptive sleeve attached to it which accommodates any sized hose by, for example, elastic, ties, Velcro, cinching bands or ties just to name a few exemplary attaching mechanisms.

Figure 7:
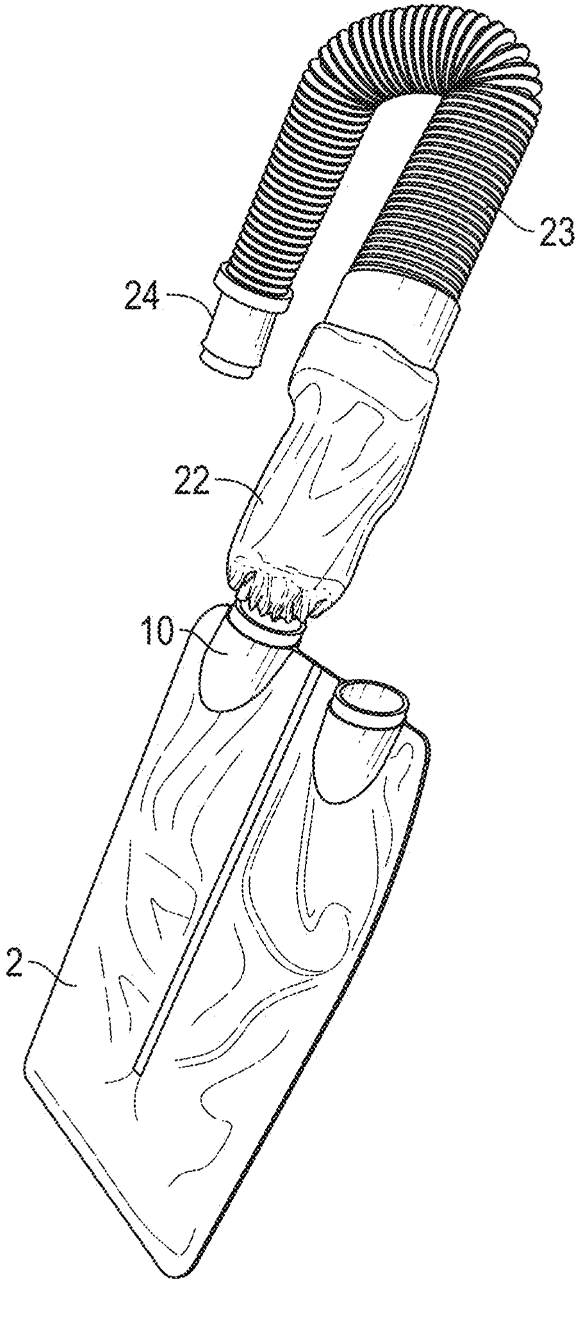
FIG. 7 shows an adjustable coupling sleeve that can be used to couple various sized conduits to the inlet or outlet of a thermal regulation enclosure.
Figure 8:
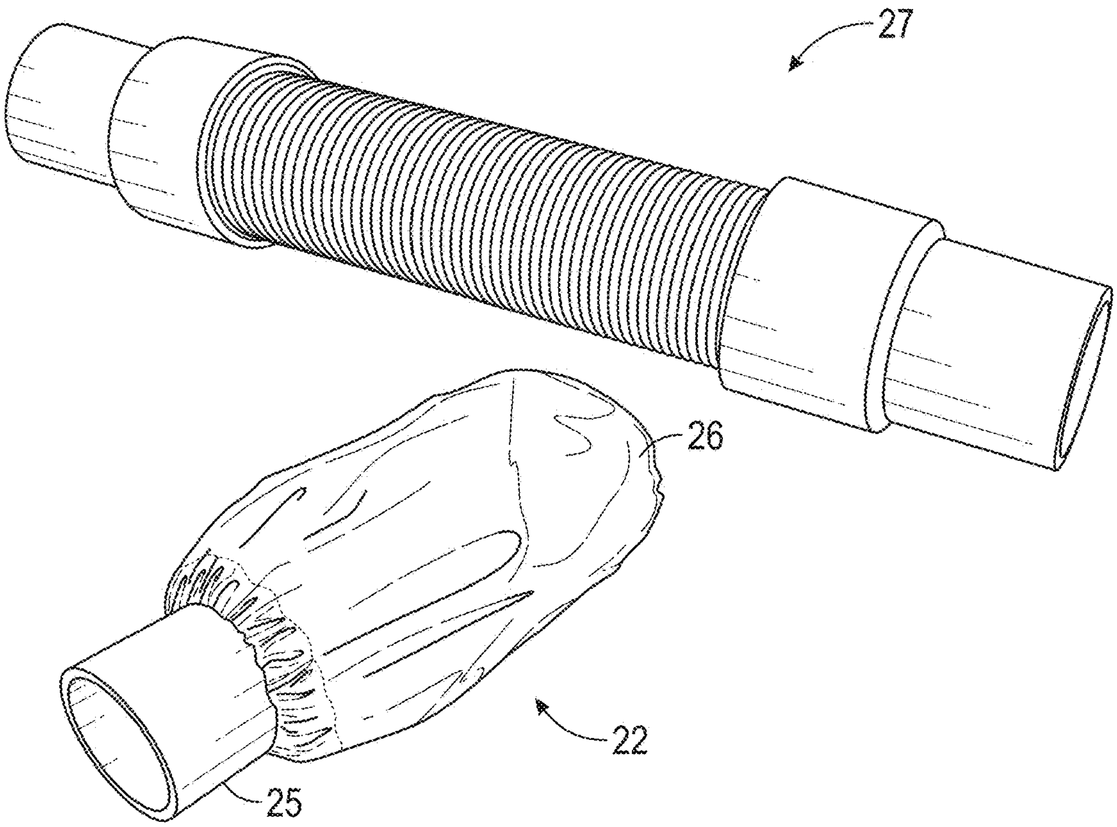
FIG. 8 shows an exemplary conduit and coupling sleeve.

FIG. 7 shows an exemplary adaptor sleeve 22 that couples a conduit 23 to a port 10 of a pad 2. The sleeve 22 can have elastic cuffs at either end, or at least one end, to allow it to stretch to fit any sized conduit end piece. As shown, the conduit 23 has a small end piece 24 on one end, and a large end piece at the other end that is inside the adaptor sleeve 22. The smaller end piece 24 could also be accommodated by the adaptor sleeve by way of the elastic cuff shrinking down to fit it. FIG. 8 shows the adaptor sleeve 22 with a fixed coupler 25 at one end to fit the port 10 and an elastic cuff 26 at the other end. An exemplary conduit 27 is also shown.

Other forced air warming systems may require that each particular type of warm air blower be accompanied by that a specific corresponding disposable warming blanket because each disposable blanket has an inlet port that only accommodates a specific size and shape of hose or cuff diameter. However, the disclosed technology is not so limited, and some embodiments can accommodate any type or diameter of warm air blower hose or cuff.

The disclosed systems can warm the patient by direct contact of the superior external surface of the pad with the dependent portion of the patient's body which is laying upon it. Warm air can be forced through the internal medium or material of the pad thereby warming the external surface of the pad. This heat from the forced warm air can therefore be transferred directly to the overlying patient. Since the surfaces of the pad are flexible, the forced warm air may tend to balloon the superior external surface of the pad to contact the patient according to the contours of the patient's anatomy, thereby providing direct heat to the overlying patient anatomy. The disclosed systems can avoid or restrict mixing of egressing air with ambient air surrounding the patient, as occurs in other systems where air egresses through small holes in the outer layer, since there can be instead direct contact of the surface of the superior surface of the pad with the overlying patient anatomy. The disclosed technology can, therefore, encompass any contained air passage with an inlet and outlet, without the holes on the patient surface, which conducts heat or potentially cool temperature to the overlying or underlying patient.

The dependent aspect of the patient, when laying on an operating table, is the largest area of the body that has never been utilized for patient warm air warming. The most common dependent position is the supine position with the posterior or dorsal aspect of the patient in contact with the superior surface of the operating table. The average total body surface area of the average American female is 2,480 square inches with the posterior aspect of the female's body being approximately 842 square inches. The average total body surface area of the average American male is 2,945 square inches with the posterior aspect of the male's body being approximately 1000 square inches. The 842 square inches of the posterior aspect of the female's body and the 1000 square inches of the posterior aspect of the male's body is a significant amount of area that has never previously been utilized for forced air warming. This posterior area is difficult to determine in animals since there are so many different sizes and body surface areas. The disclosed technology, therefore, can provide for a new and significant opportunity for heat transfer to a large area of the patient's anatomy which has never been previously utilized with forced air warming.

In embodiments where the exterior surfaces of the pad is impervious to air, no non-sterile air can contact an open surgical wound as can occur with forced air blankets that have multiple pin holes on the patient surface to allow egress of warm air. The inlet air, after making its circuitous journey through the interior of the pad can have only one outlet (in other embodiments, two or more inlets or outlets can be included). This outlet can be so designed or attachments to the outlet so designed that the exiting air is directed away from the surgical wound. By this manner the exiting air can also be directed so that it does not interfere with the laminar flow of sterile air in the room.

Some embodiments can be utilized as a warming/cooling pad upon which the patient may lay to provide warming/cooling to the underside, posterior or dependent aspect of the patient. The patient may be positioned in the prone, supine, lateral or any partial prone, supine or lateral positions on the pad. The area of the body contacting the pad will be the dependent aspect of the patient. The patient's body can, therefore be placed in any of these positions on the pad which can be placed, for example, on the surface of an operating table, a preoperative surface, postoperative surface, infant incubators, on surfaces of imaging equipment such as X-ray, CT scanners and MRI scanners as well as any patient positioning devices to name only a few areas of utility.

Figure 9:
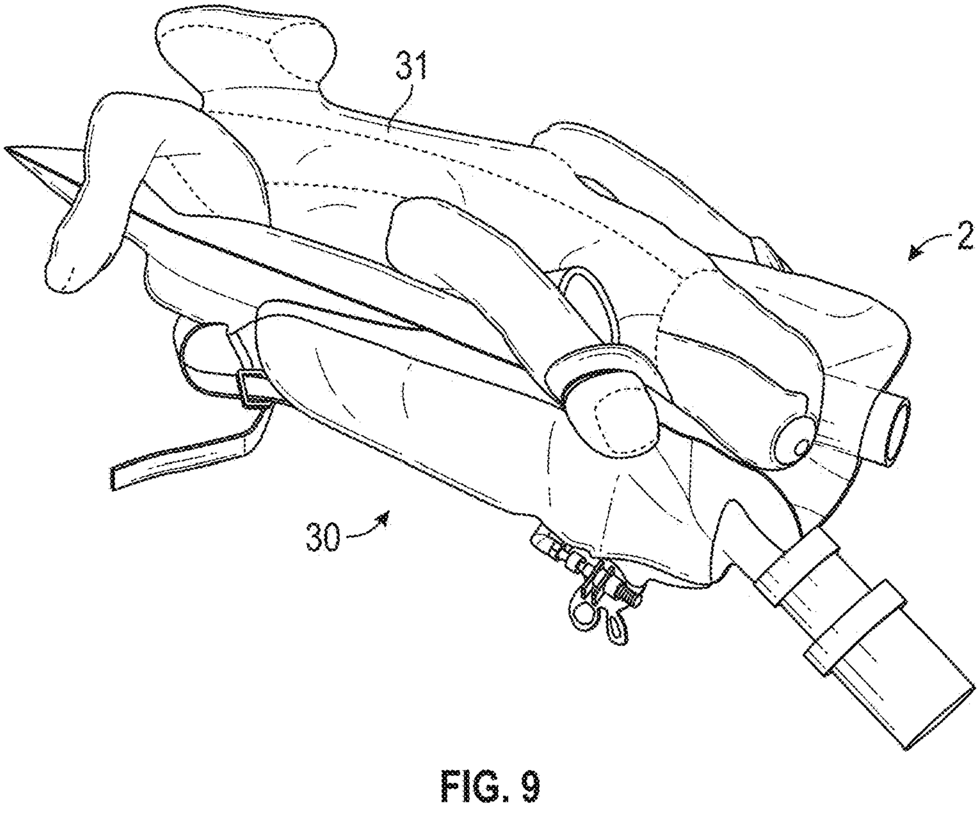
FIG. 9 shows an exemplary thermal regulation enclosure used in conjunction with a patient positioning device to hold a veterinary patient in a desired position while regulating its temperature during a surgical procedure.
Figure 10:
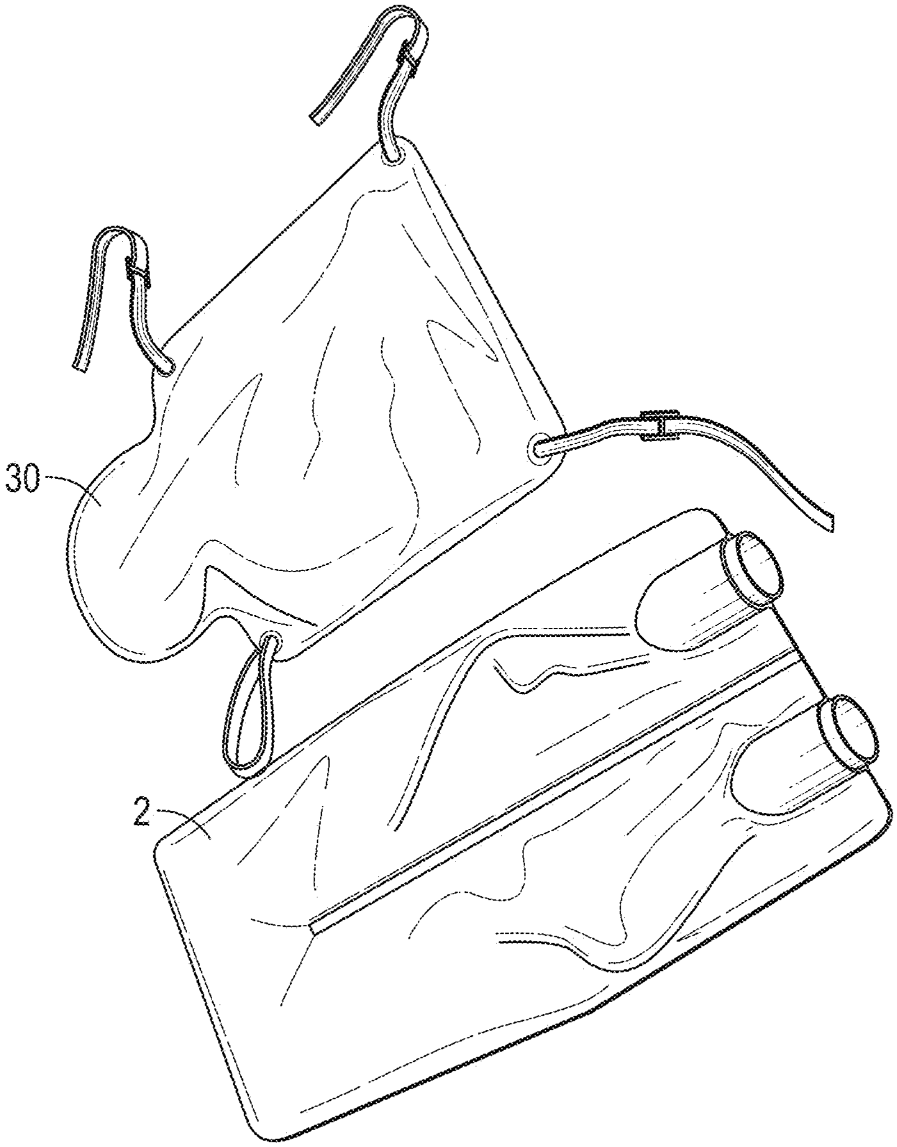
FIG. 10 shows the thermal regulation enclosure and the patient positioning device of FIG. 9 side-by-side.

FIG. 9 shows an example where a pad 2 is used with a patient positioning device (e.g., an air-evacuatable positioner or vacuum activated positioner) 30 that holds a patient 31 is a desired position. In this example, the patient is held with its belly up with the pad 2 between the patient 31 and the positioner 30. FIG. 10 shows the pad 2 and the positioner 30 separately. In some examples, the pad may be constructed so that the pad is designed in the shape of a positioner that may be holding the patient in the appropriate position for surgery. It can also be designed so that it can be taken off or out of the positioning device and is independent of the positioning device (like in FIG. 10). The pad can also be made an integral part of a positioning device which holds the patient, for example, for operative procedures preoperatively, intraoperatively and postoperatively as well as imaging these being only a few examples. In some examples, the pad has been integrally manufactured on the patient surface. This can be done, for example, by gluing, sewing, stapling, Radio Frequency welding, and other adherents, dependent on the type of material of which the positioner and warming pad are comprised.

Since the warm air coming out of the outlet is of similar temperature as the warm air going into the inlet, it is possible to utilize this warm air from the outlet to be used in series with another similar pad, such as on the contra-lateral, opposite, lateral or superior aspect of the patient. For example, two warming pads can be connected in series by a flexible conduit by connecting the outlet port of one pad to the inlet port of the other. For example, the outlet port from the pad underneath a patient can be connected by a flexible conduit to the inlet port of a pad overlying the chest and upper extremities of the patient were the patient laying in the supine position. A disposable warming blanket with multiple pin sized holes that is commercially available can also be connected in like manner. For example, a warming pad as herein disclosed can be underneath the patient with a connecting hose coming out of its outlet with the other end of the connecting hose connected to the inlet of the disposable blanket which is overlying the patient, or another one of the warming pads, so that the patient is now warmed from above and below.

Figure 11:
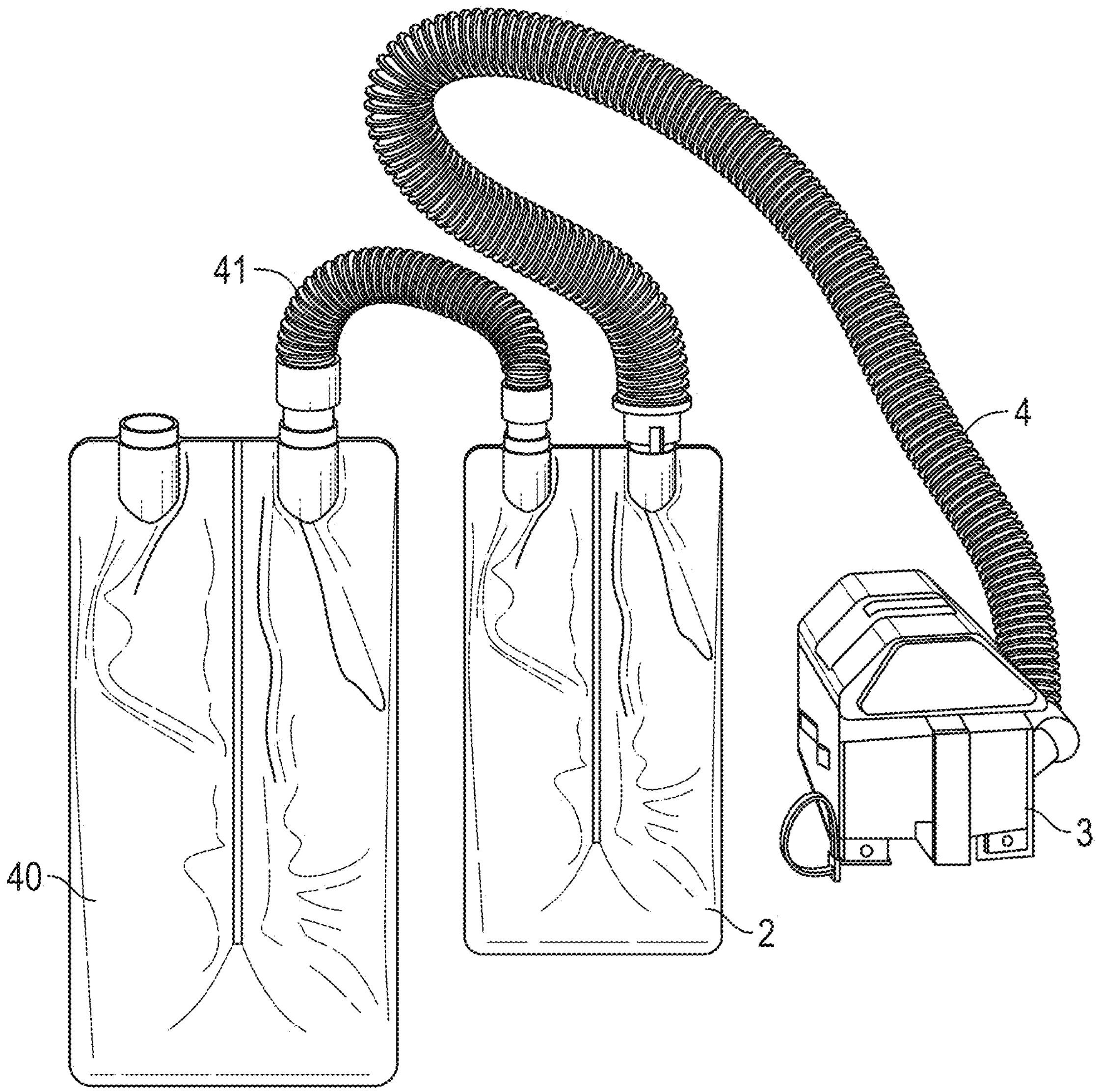
FIG. 11 shows a system comprising two thermal regulation enclosures coupled in series with an air blower and two conduits.
Figure 12:
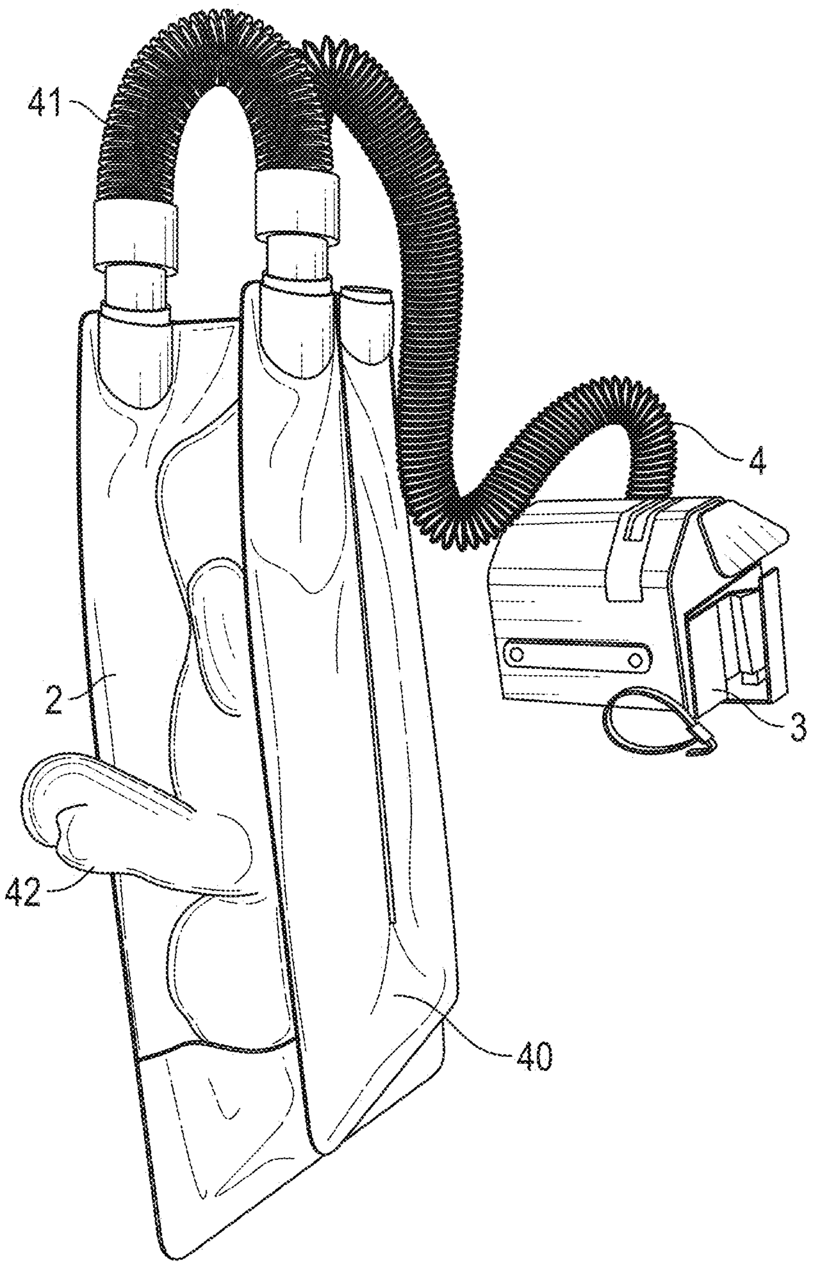
FIG. 12 shows the system of FIG. 11 in use with a patient, with one enclosure below the patient and one enclosure over the patient.

FIG. 11 shows an exemplary system that includes an air blower 3 coupled to a conduit 4 that is coupled to an inlet of a pad 2. The outlet of the pad 2 is coupled to a second conduit 41 (which can be the conduit 27 of FIG. 8 for example), which is coupled to an inlet of a second pad 40. Air then exits an outlet port of the second pad 40. FIG. 12 shows the system of FIG. 11 with the first pad 2 under a patient 42, and the second pad 40 over the patient.

Two of the pads can also be connected to a forced air blower in parallel by means of a “Y” connector or other splitter. In this manner a hose from the blower connects to the Y connector and from the two limbs of the Y connector a connecting pipe or tube connects to the inlet of two separate pads. This configuration may be utilized for warming above and below the patient or when a warming area above or below the patient needs to be enlarged.

The inlet and outlet ports of the pads may be of the same diameter so that there can be interchangeability of the ports as clinical use dictates. This is, however, not necessary for function of the device. Different diameters of cuffs or blower hoses may be utilized if they match the accommodating diameters of the inlet or outlet ports. If the inlet and outlet ports are made of flexible or elastic sleeves or invaginations any diameter of blower hose or series connecting conduits can be utilized.

A disposable or non-disposable slipcover may be designed to protect the pad and to prevent cross contamination between patients. This slipcover would be made in the general shape of the pad and accommodations made for the inlet and outlet ports or sleeves. This slipcover can be removed after patient use and either disposed of or cleaned. The slipcover can be made of various materials some of which would be paper, nonwoven fabrics with a sealable liner, various plastics and vinyl just to name a few. These materials can be sewn, welded, heat sealed, glued, Velcroed, just to name a few processes by which the seams or material approximations of the slipcover could be made.

The pad may also be constructed so that during the manufacture of three dimensional fabric (3D fabric) or other materials and the exterior shell becomes directly adhered to the 3D fabric and encloses this 3D fabric as well as separations in the 3D fabric to create air channels that allow for airflow throughout the interior of the 3D fabric and allow for an inlet and outlet of airflow.

The material of the air-flow layer in the internal aspect of the pad can be resistant to crushing and also flexible or supple enough that soft tissue injuries are not sustained by laying on the pad for prolonged periods of time. To determine this resistance to crushing, one can measure the pounds per square inch that can be applied to the material before it begins to crush. For this crush-resistance analysis, the patient laying on the pad is assumed to be laying in the supine position with its posterior aspect in direct contact with the pad. The anterior and the lateral aspects of the patient would be excluded from this contact. The average human exerts approximately 0.20 pounds per square inch of downward pressure or force when laying supine on a flat surface. This is calculated as follows:

| Patient, Patient Surface | Surface Area | Weight, (Pressure) |
|---|---|---|
| Average Adult American female | 2,480 sq. in. | 170 lbs |
| Average Adult American female posterior | 842 sq. in. | (170 lbs/842 sq. in.) = 0.20 |
| Average Adult American male | 2,945 sq. in. | 198 lbs |
| Average Adult American male posterior | 1,000 sq. in. | (198 lbs/1000 sq. in.) = 0.198 |

The ability of the underlying material to withstand approximately 0.20 pounds per square inch of downward pressure by the patient's body weight without being crushed can allow for the patient's body to be upheld while allowing for movement of air through the cross-section of the material and, therefore, underneath the patient's body. The pounds per square inch of downward pressure of an animal's body is likely similar to that of a human, however, the weight and surface areas between various animals varies because of the differences in body surface area to mass ratios between animals.

Testing of two types of material was performed by placing a 2 inch by 2 inch flat block on the flat surface of each material and loading it with weight until compression of the material occurred in which a cross sectional space was no longer present as in the accompanying picture. Material A is a 3 dimensional fabric in which there are upright filaments or fibers which support the patient's weight. Material B which is a plastic mesh in which the majority of the fibers are oriented in a horizontal direction.

Material A compressed at 2.75 lbs. per square inch

Material B compressed at 1.36 lbs. per square inch

Both Materials A and B would be suitable for use in the disclosed pads since both have compressibility resistance greater than that of 0.20 lbs. per square inch. Material A, however, allows for greater margin of compressibility.

With regard to 3D fabric, the thickness or height of the fabric can be determined by the length the upright fibers that compose the height. The density and the length of these fibers can determine the compressibility of the fabric when a weight is applied to the surface of the fabric. The longer the fibers and the less dense the fibers the greater the compressibility of the fabric when a weight is applied to its surface. When the fibers are shorter and have greater density there will be less compression when a weight is applied to the surface of the fabric. It can be desirable to have a medium underneath the patient that will hold up the weight of the patient and allow warm air to be moved under the entire underside of the patient and also have the surface upon which the patient is laying to be sufficiently compressible so that pressure sores do not occur on the patient's skin surface adjacent to the 3D fabric. Therefore, the disclosed technology can include a 3D fabric with relatively short and dense fibers that will hold up the weight of the patient and allow air to be moved under the entire body of the patient. Superior to this 3D fabric, with shorter denser fibers, can be positioned a 3D fabric with longer fibers that are more compressible and conform to the contours of the patient's body that is contacting the superior surface of the 3D fabric with the longer fibers (see the attached drawings).

Any of the devices, systems, and methods disclosed herein can also be used for patient cooling instead of patient warming by conducting cool air through the pad instead of warm air. In addition, other fluids can be used instead of air for warming or cooling, such as other gasses (e.g., nitrogen, carbon dioxide, mixtures of gases, etc.) or liquids (e.g., water, high thermal capacity liquids, etc.). In some embodiments, the functional fluid used can be conducted in a loop, such that the fluid is contained in a controlled environment and cannot contact the patient or escape into the ambient air. In some embodiments, the fluid be sourced from a controlled source (e.g., a sterile source), such as from a container or from another room. In some embodiments, the exiting fluid can be sent to a container or to another room or outside. In some embodiments, the working fluid can be cleaned or sterilized after exiting, prior to being released into the ambient air or recycled.

A material resistant to crushing can be defined as a material when weight or pressure is placed thereupon, the superior and dependent surfaces do not completely contact each other or the superior surface upon which the weight or pressure is imposed will be minimally or not at all indented or flexed. This allows for air flow between the superior and dependent surfaces at minimal or decreased resistance.

Embodiments of the disclosed technology can also be utilized for cooling a patient. In this situation a unit as described can be placed underneath the patient as well as a unit above the patient if necessary and attached to a cold air source to blow cold air underneath the patient and also above the patient to provide cooling. These units can be attached to cold air sources individually/independently to use several cool air sources or in series to use one cold air source. This can be used in cardiac surgery were patient cooling is necessary and after the surgery is complete the same system can be attached to a warm air source to rewarm the patient. Cooling, using the disclosed technology, could also be utilized when a critically ill patient with cardiac or neurological injury needs to be cooled to decrease the body's metabolic demands.

The technology described herein has multiple functional use modes. For example, it may be utilized on an operating table, emergency or ambulance gurney and emergency patient stabilizing backboards.

Figure 15:
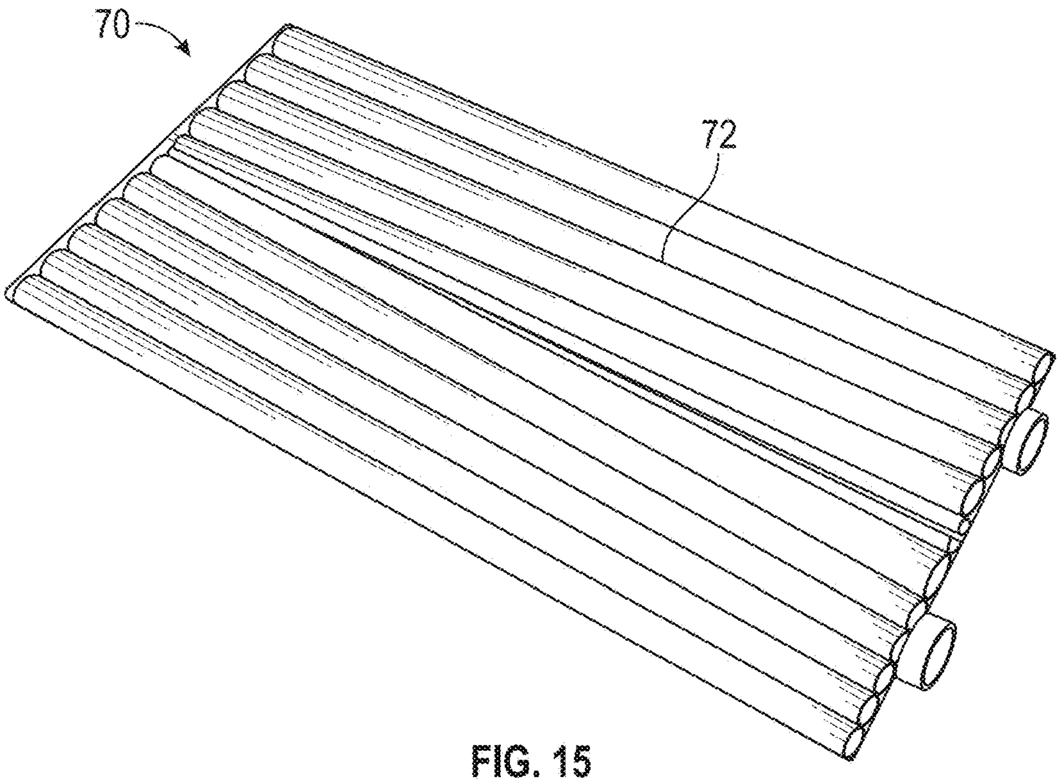
FIG. 15 shows an exemplary thermal regulation enclosure that includes an air inlet and an air outlet and several longitudinal creases.
Figure 16:
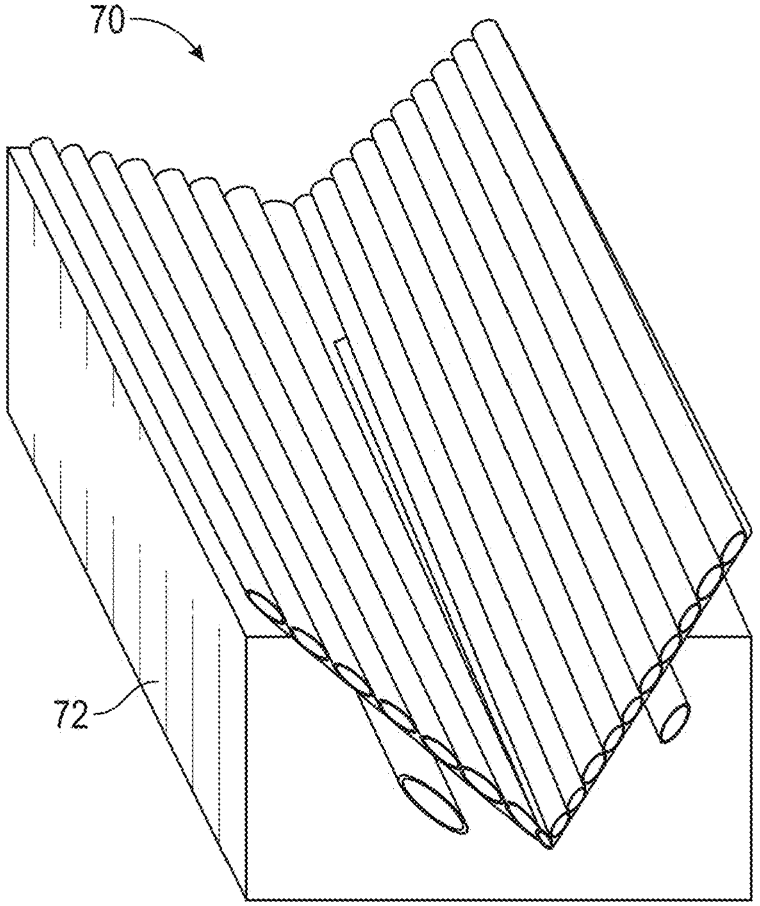
FIG. 16 shows the enclosure of FIG. 15 folded along a longitudinal crease to conform with the shape of a V-shaped patient positioning system.
Figure 17:
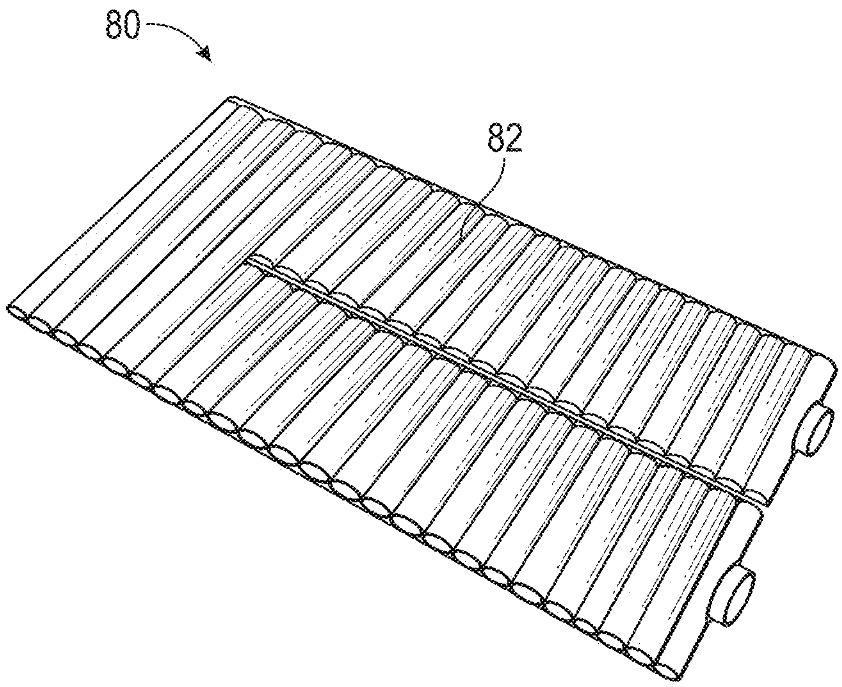
FIG. 17 shows an exemplary thermal regulation enclosure that includes an air inlet and an air outlet and several lateral creases.
Figure 18:
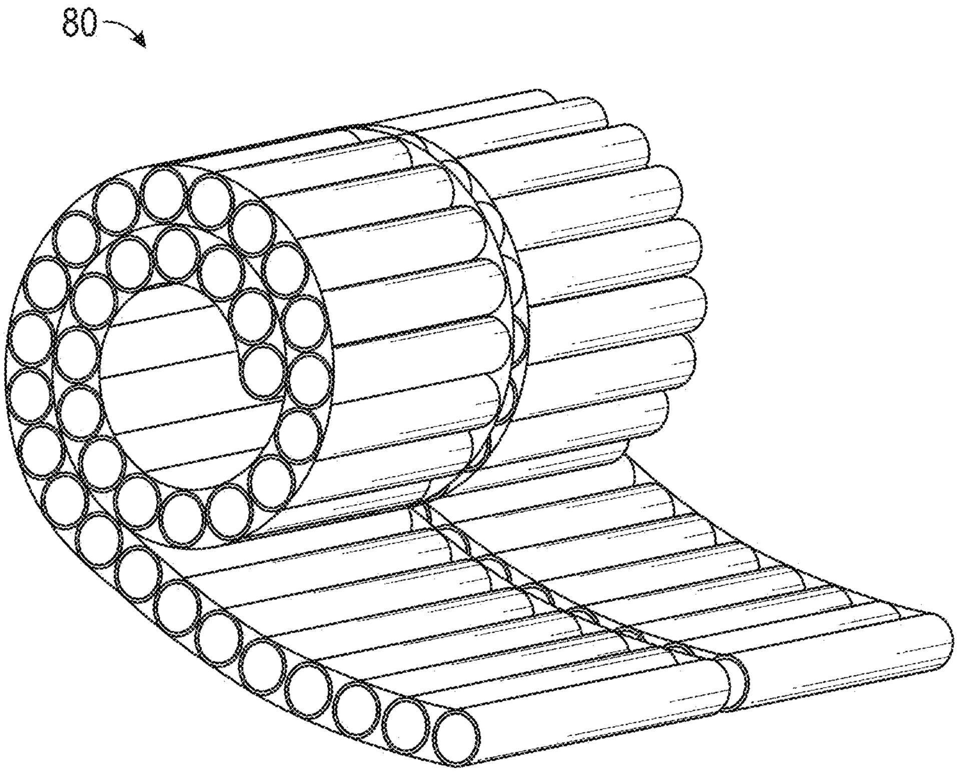
FIG. 18 shows the enclosure of FIG. 17 rolled up using the lateral creases.

The internal and/or external materials of the pad can be made in a fashion in which pattern or construction features of the material lend themselves to certain orientations in the pad to accommodate differing clinical situations or uses. For example, materials with corrugations or rows of tubular shapes, or other shapes, may lend themselves to a longitudinal orientation in some clinical situations. FIG. 15 shows an exemplary pad 70 that includes longitudinal rows of tubular shapes 72. Air flow is allowed to flow transverse to the rows of tubular shapes, from one row to the next row, to allow air to flow through the whole enclosure from the inlet to the outlet. The tubular shapes can be partial baffles or can be formed by shaping the internal materials. If lateral warming of the patient is needed or flexing of the invention unit is needed longitudinally, as for example in a V trough patient positioner or vacuum activated patient positioner, it may be preferable for the internal material to be longitudinally oriented as shown in FIG. 16. While it may be preferable to have a longitudinal orientation in one clinical or functional situation, in other situation it may be preferable to have a cross wise orientation in other clinical or functional situation. FIG. 17 shows an exemplary pad 80 that has lateral or cross-wise tubular shapes 82 that allow it to roll, as shown in FIG. 18. This can be desirable, for example, when the pad is required to lay flat on a lengthy surface such as a six to seven foot long operating table. In this situation, the cross-wise orientation in addition to under body warming also provides for stability of the patient's body on the operating table. Additionally, the cross wise orientation may accommodate the ability for the pad to be rolled up into a compact roll to provide for greater convenience in storage and shipping.

Figure 19:
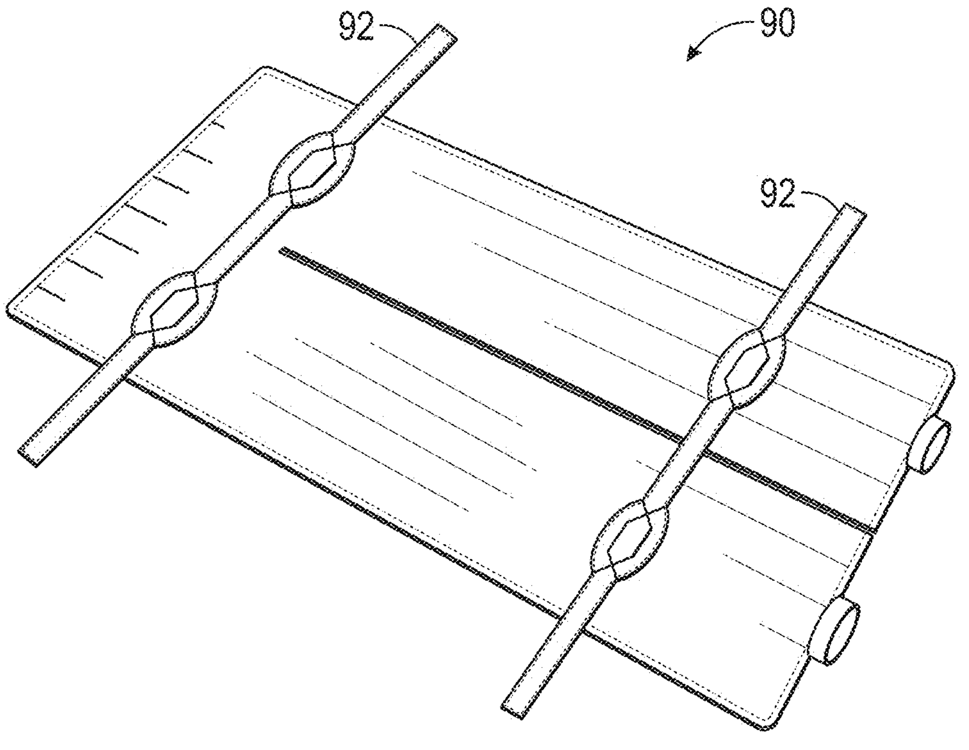
FIG. 19 shows an exemplary thermal regulation enclosure that includes straps coupled to one side for securing the enclosure to a table or other underlying support surface.
Figure 20:
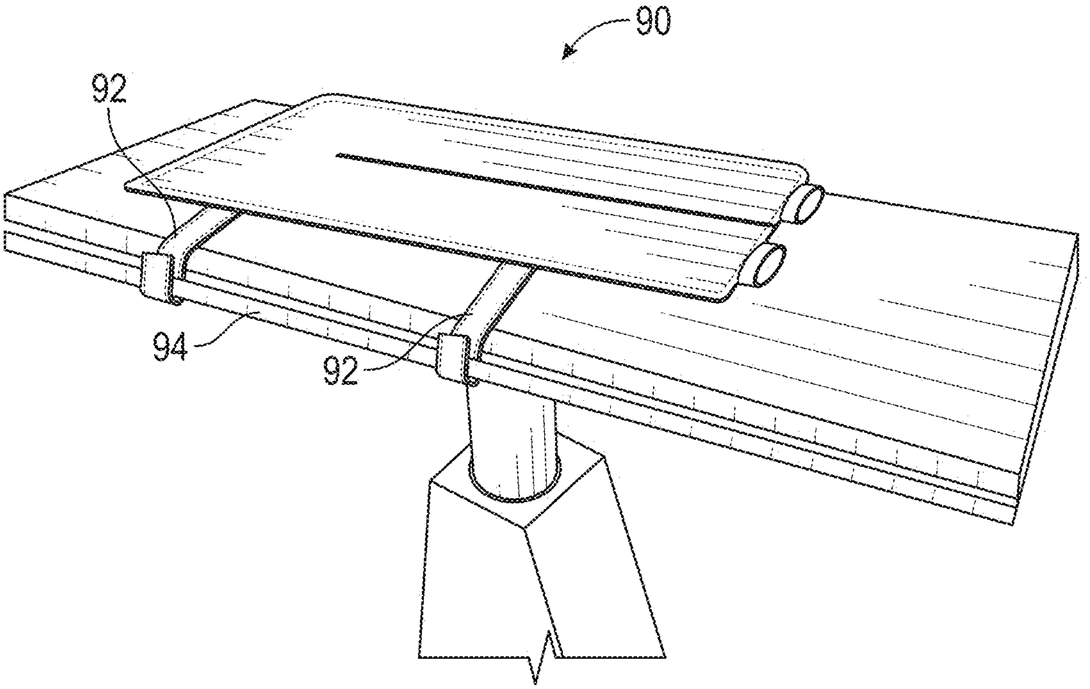
FIG. 20 shows the enclosure of FIG. 19 secured to a surgical table using the straps.

In some embodiments, it can be beneficial to have attachments to the underlying surface to prevent movement of the pad when the patient is being placed thereupon or when it is necessary for the stable maintenance of the patient on the underlying surface. FIGS. 19 and 20 illustrate an embodiment 90 that includes straps 92 attached to one side of the pad for coupling the pad to rails 94 of an operating table (or other support surface). For example, this attachment can be used for attachment to an operating table, patient transport gurney, emergency patient transport gurney or patient support devices. This can be accomplished for example, with straps or bands of a sufficiently strong material which are attached to the pad and in turn attached to the supporting surface. These attachments can be, for example, be sewn, glued, heat sealed, welded or riveted just to mention a few attachment methods. These attachments can be attached to the pad on the lateral aspect, head end, foot end, underside or superior side. There can also be an adherence of the undersurface of the pad to the superior surface of the supporting surface. This can be accomplished for example by permanent or partially permanent adhesives or by complimentary Velcro adherents on the underside of the pad and the superior aspect of the supporting surface. Some attachment embodiments may be manufactured as an integral part of the external material.

Figure 21:
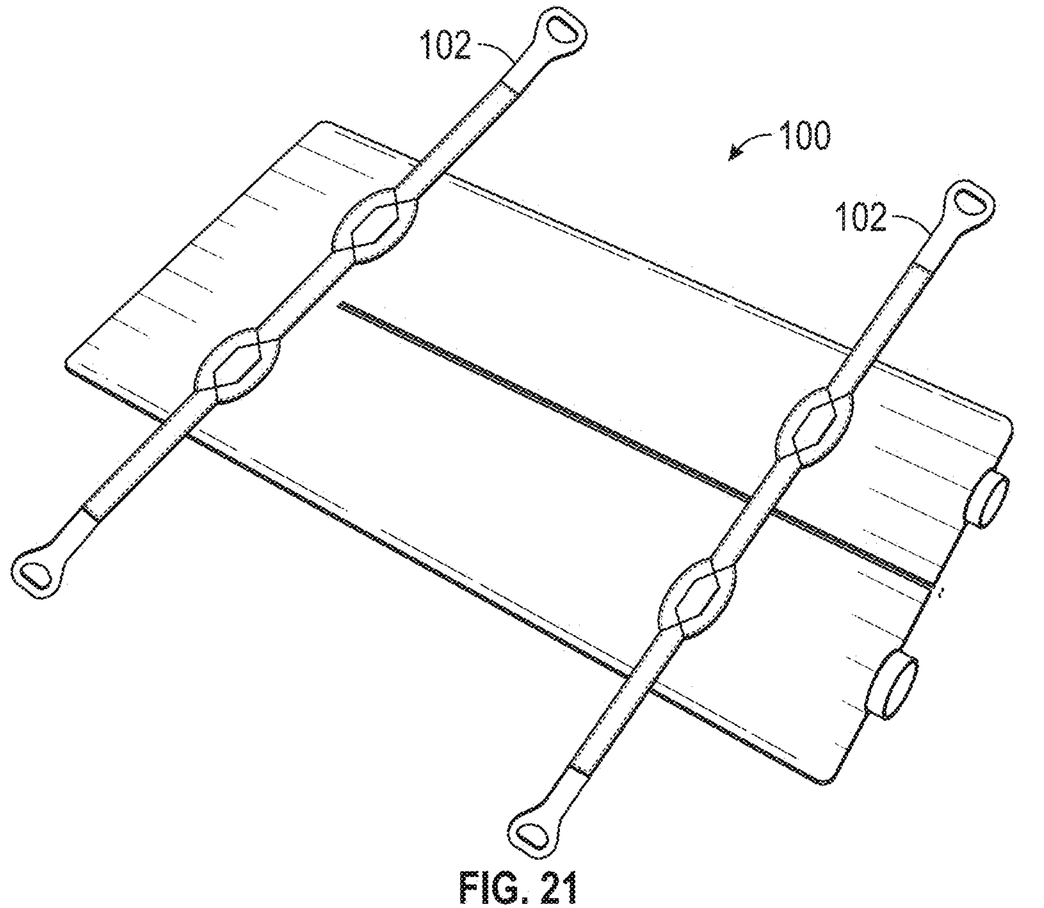
FIG. 21 shows an exemplary thermal regulation enclosure that includes straps coupled to one side, where the straps include handles for lifting the enclosure.
Figure 22:
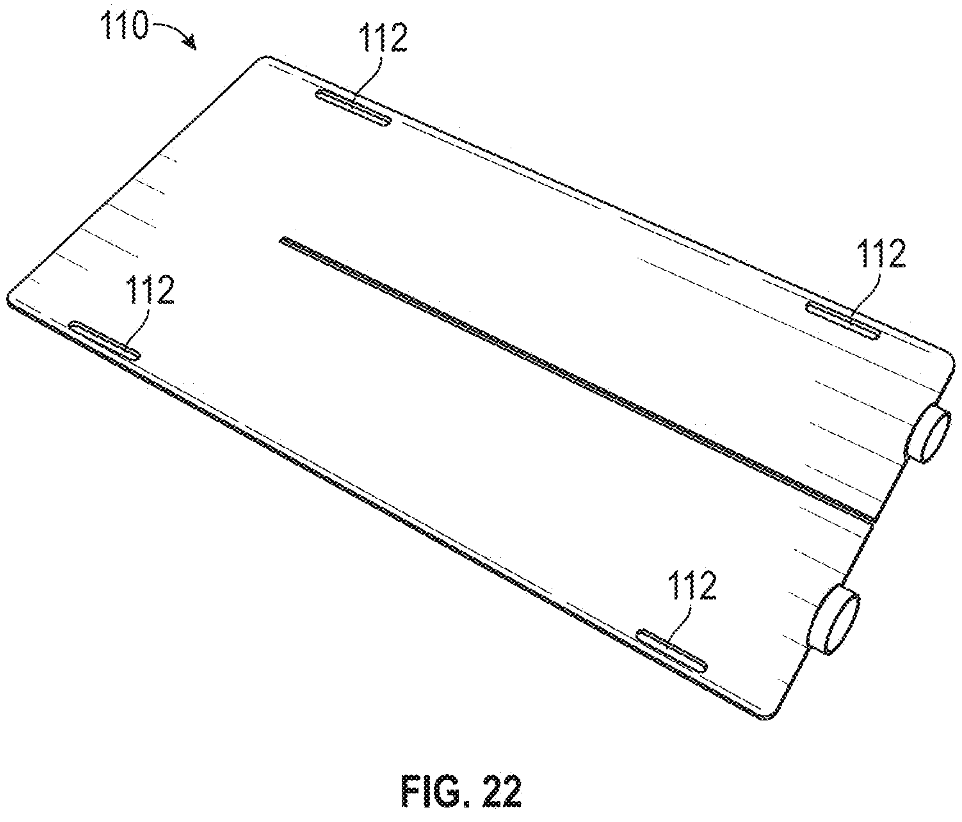
FIG. 22 shows an exemplary thermal regulation enclosure that includes hand holes in the lateral sides of the enclosure.

Embodiments of the pad can also include handles which are either attached directly to the pad or to straps or other adherents to the pad. The handles can be single or multiple. These handles can be placed on one side only or on both sides opposite each other or on the ends singly or one or more handles on each end opposite each other. FIG. 21 shows an exemplary pad 100 that includes straps with handles 102 attached to one side. Handles can also be an integral part of the exterior material of the invention unit itself. FIG. 22 shows an exemplary pad 110 that includes integral handles 112. These handles would serve to move the pad itself onto or off the supporting surface and to move the patient which is on the pad to another supporting surface.

Figure 13:
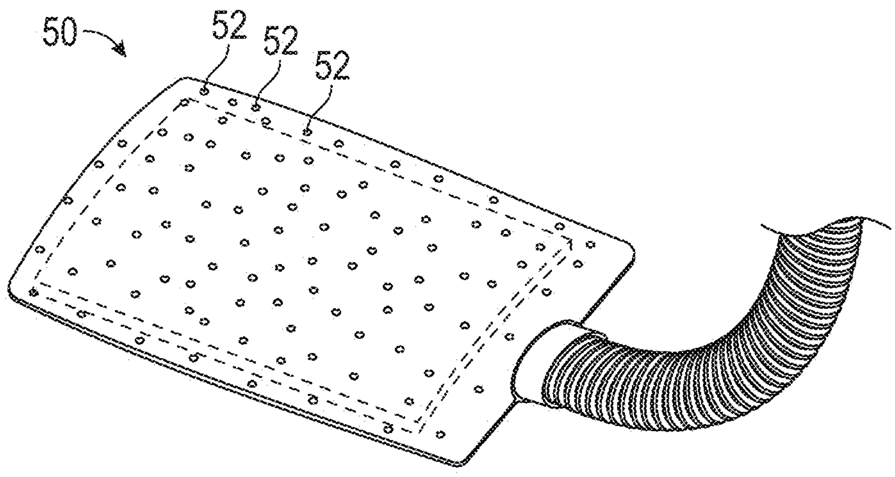
FIG. 13 shows an exemplary thermal regulation enclosure that includes an air inlet and many small air outlet holes on one side.
Figure 14:
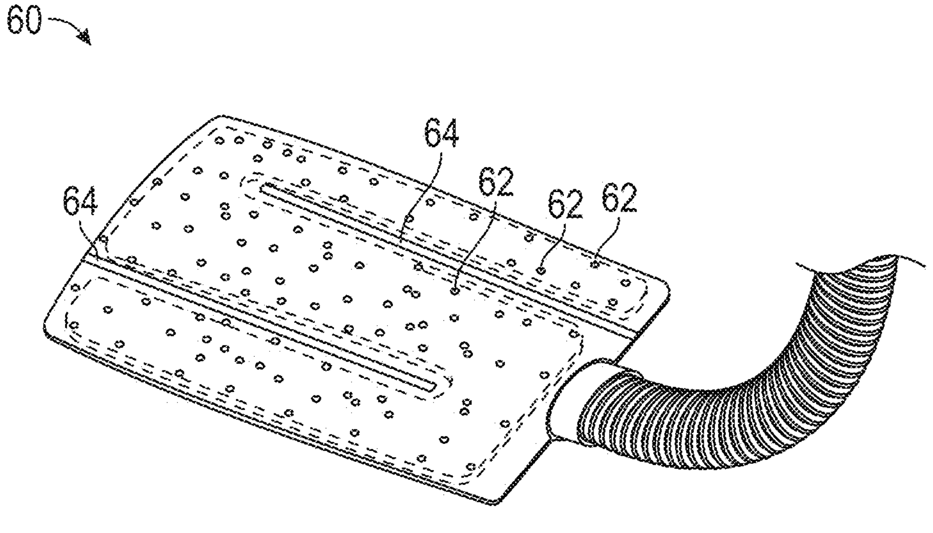
FIG. 14 shows an exemplary thermal regulation enclosure that includes an air inlet and many small air outlet holes on one side, as well as baffles that direct the air flow inside the enclosure.

Other embodiments can have an air and fluid permeable material on one or both external surfaces of the pad. The permeable external surfaces for example only, could be porous fabric, paper with multiple pin sized holes, non-woven fabrics with or without pin sized holes, woven fabrics, plastic sheet with pin sized holes to name only a few. The surfaces could be sealed around the perimeter for example only, with sewing, gluing, welding, heat sealing, to name only a few adhering methods. The surface immediately adjacent to the patient would be material which is permeable to air. The material immediately adjacent to the underlying surface may or may not be permeable to air. There may also be partitions or baffles made in the external material for directing the inlet air throughout the interior which can be made for example, by sewing, gluing, welding, heat sealing or other adhering methods to direct air throughout the interior of the pad. There can also be embodiments in which there are no partitions or baffles to direct the inlet air throughout the interior. FIG. 13 illustrates an exemplary pad 50 that includes no baffles or partitions and includes plural holes 52 for air egress on one surface. FIG. 14 illustrates an exemplary pad 60 that includes baffles 64 and air egress holes 62. In such embodiments, the interior can have material which is completely or partially resistant to crushing with pressure or patient weight, to allow for air flow under or around the patient at minimal resistance or back pressure. The internal material can be configured or cut to match the shape, contours and partitions in the external materials. This embodiment can have an inlet allowing air from an air blowing source into the pad and the exit of the air through the air permeable external surface or surfaces. The air inlet can be situated on any side or surface of the pad that provides the best clinical advantage. The inlet can be a pipe which compliments the air hose diameter from the warm air source or it could be an elastic sleeve, draw string sleeve, invagination of the external material to name a few inlet attachments. Such embodiments can be utilized when the patient is placed thereupon in situations in which air blowing around the patient would not contaminate a sterile field or otherwise impair the potential health of the patient. This embodiment can provide for underbody warming of the patient as well as warm air exiting from the permeable surface of the pad around the lateral aspects of the patient. This warm air exiting from the air permeable surface can be allowed to flow to the ambient atmosphere or could be trapped by an overlying blanket to provide greater warming efficiency. This embodiment can be well utilized in the preoperative and postoperative warming of the patient.

For purposes of this description, certain aspects, advantages, and novel features of the embodiments of the inventive technology are described herein. The disclosed apparatuses, systems, and methods should not be construed as limiting in any way. Instead, the present disclosure encompasses all novel and nonobvious features and aspects of the various disclosed embodiments, alone and in various combinations and sub-combinations with one another. The disclosed embodiments are not limited to any specific aspect or feature or combination thereof, nor do the disclosed embodiments require that any one or more specific advantages be present or problems be solved.

As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means mechanically, chemically, electrically, magnetically or otherwise coupled or linked and does not exclude the presence of intermediate elements between the coupled items, unless otherwise described herein.

In view of the many possible embodiments to which the principles disclosed herein may be applied, it should be recognized that the illustrated embodiments are only examples and should not be taken as limiting the scope of the disclosure. Rather, the scope of the disclosure is intended to be at least as broad as the full scope of the claims and their equivalents.

The invention claimed is:

1. A patient thermal regulation system, comprising:

an air-impermeable enclosure comprising flexible air-impermeable enclosure walls, an air inlet, and air outlet, wherein an airflow pathway is defined by the flexible air-impermeable enclosure walls and extends from the air inlet to the air outlet, wherein a first enclosure wall of the flexible air-impermeable enclosure walls defines a patient-side exterior surface of the air-impermeable enclosure and a second enclosure wall of the flexible air-impermeable enclosure walls defines an opposing exterior surface of the air-impermeable enclosure relative to the patient-side exterior surface, wherein the first enclosure wall has a same thickness as the second enclosure wall;

wherein the patient thermal regulation system is configured to have air flow in through the air inlet, along the airflow pathway, and out through the air outlet, such that heat is transferred through the first enclosure wall between the flowing air and a patient positioned on the patient-side exterior surface of the air-impermeable enclosure;

wherein the enclosure comprises at least one baffle connecting the first and second enclosure walls, wherein the at least one baffle defines a circuitous air channel for the airflow pathway, and wherein the circuitous air channel comprises a first longitudinally extending channel in communication with the air inlet, a second longitudinally extending channel in communication with the air outlet, and a laterally extending channel extending between the first longitudinally extending channel and the second longitudinally extending channel.

2. The system of claim 1, wherein the first enclosure wall is made of a same material as the second enclosure wall.

3. The system of claim 1, wherein the at least one baffle is exactly one baffle.

4. The system of claim 1, wherein the circuitous air channel consists of the first longitudinally extending channel, the second longitudinally extending channel, and the laterally extending channel.

5. The system of claim 1, wherein the at least one baffle is formed via one or more of a heat seal or a radio frequency weld between the first enclosure wall and the second enclosure wall.

6. The system of claim 1, wherein the air inlet comprises a first conduit and the air outlet comprises a second conduit, wherein a longitudinal axis of the first conduit is parallel to a longitudinal axis of the first longitudinally extending channel, and wherein a longitudinal axis of the second conduit is parallel to a longitudinal axis of the second longitudinally extending channel.

7. The system of claim 1, further comprising an air-flow layer positioned within the enclosure, wherein the airflow layer comprises a material having an end portion that corresponds to a shape of the laterally extending channel and two leg portions extending from the end portion, wherein the two leg portions correspond to a shape of the first and second longitudinally extending channels, and wherein material forms a plurality of air-flow channels.

8. The system of claim 1, further comprising an adapter sleeve, the adapter sleeve having a flexible body, an end piece disposed at a first end portion of the flexible body, and a cuff disposed at a second end portion of the flexible body.

9. The system of claim 8, wherein the end piece is sized and shaped to be engaged with the air inlet of the air-impermeable enclosure, wherein the cuff is configured to fit over a conduit of an air blower.

10. The system of claim 9, wherein the cuff is elastic and is configured to accommodate conduits of various sizes for coupling the air-impermeable enclosure to an air blower.

11. The system of claim 1, further comprising:

an air-flow layer positioned within the enclosure and comprising three-dimensional material having air-flow channels extending through the three-dimensional material; and a cushion layer positioned within the enclosure, wherein the cushion layer is disposed between the air-flow layer and the first enclosure wall.

12. The system of claim 11, wherein the air-flow channels extend parallel to a longitudinal axis of the enclosure.

13. The system of claim 11, wherein the air-flow layer comprises an open-cell material that forms the air-flow channels and is configured for three-dimensional flow of air through the air-flow layer.

14. A patient thermal regulation system, comprising:

an air-impermeable enclosure comprising flexible air-impermeable enclosure walls, an air inlet, and air outlet, wherein an airflow pathway is defined by the flexible air-impermeable enclosure walls and extends from the air inlet to the air outlet, wherein a first enclosure wall of the flexible air-impermeable enclosure walls defines a patient-side exterior surface of the air-impermeable enclosure and a second enclosure wall of the flexible air-impermeable enclosure walls defines an opposing exterior surface of the air-impermeable enclosure relative to the patient-side exterior surface, wherein the first enclosure wall is made from a same material as the second enclosure wall;

wherein the patient thermal regulation system is configured to have air flow in through the air inlet, along the airflow pathway, and out through the air outlet, such that heat is transferred through the first enclosure wall between the flowing air and a patient positioned on an exterior surface of the air-impermeable enclosure;

wherein the enclosure comprises at least one baffle connecting the first and second enclosure walls, and wherein the at least one baffle is formed via one or more of a heat seal or a radio frequency weld between the first enclosure wall and the second enclosure wall;

wherein the at least one baffle is exactly one baffle;

wherein the baffle defines a circuitous air channel for the airflow pathway, and wherein the circuitous air channel is formed by a first longitudinally extending channel in communication with the air inlet, a second longitudinally extending channel in communication with the air outlet, and a laterally extending channel extending between the first longitudinally extending channel and the second longitudinally extending channel.

15. A patient thermal regulation system, comprising:

an air-impermeable enclosure comprising flexible air-impermeable enclosure walls, an air inlet, and air outlet, wherein a first enclosure wall of the flexible air-impermeable enclosure walls defines a patient-side exterior surface of the air-impermeable enclosure and a second enclosure wall of the flexible air-impermeable enclosure walls defines an opposing surface of the air-impermeable enclosure relative to the patient-side exterior surface, wherein the first enclosure wall is attached to the second enclosure wall via one or more of a heat seal or a radio frequency weld to form a baffle, and wherein a circuitous airflow pathway is defined by the first enclosure wall, the second enclosure wall, and the baffle and extends from the air inlet to the air outlet;

wherein the patient thermal regulation system is configured to have air flow in through the air inlet, along the circuitous airflow pathway, and out through the air outlet, such that heat is transferred through the first enclosure wall between the flowing air and a patient positioned on the patient-side exterior surface of the air-impermeable enclosure; and wherein the circuitous air pathway consists of a first longitudinally extending channel in communication with the air inlet, a second longitudinally extending channel in communication with the air outlet, and a laterally extending channel extending between the first longitudinally extending channel and the second longitudinally extending channel.

* * * * *